United States Patent
Andes et al.

[11] Patent Number: 5,858,078
[45] Date of Patent: Jan. 12, 1999

[54] PLATELET-SHAPED TITANIUM DIOXIDE PIGMENT

[75] Inventors: Stefanie Andes, Maintal; Gerd Bauer, Kleinostheim; Günter Brenner, Griesheim; Dieter Brückner, Darmstadt; Andrea Heyland, Ober-Kainsbach; Matthias Kuntz, Seeheim; Karl Osterried, Dieburg; Gerhard Pfaff, Münster; Michael Schmelz, Kriftel, all of Germany

[73] Assignee: Merck Patent Gesellschaft mit Beschrankter Haftung, Germany

[21] Appl. No.: 983,346

[22] Filed: Jan. 9, 1998

[30] Foreign Application Priority Data

May 9, 1996 [DE] Germany .................. 196 18 564.5

[51] Int. Cl.⁶ ................................................. C09C 1/36
[52] U.S. Cl. .......................... 106/437; 106/415; 106/436
[58] Field of Search ............................ 106/415, 436, 106/437

[56] References Cited

U.S. PATENT DOCUMENTS

| | | | |
|---|---|---|---|
| 3,138,475 | 6/1964 | Schroder et al. | 106/415 |
| 3,340,006 | 9/1967 | Mochel | 423/592 |
| 3,395,203 | 7/1968 | Morita | 264/141 |
| 3,582,382 | 6/1971 | Watanabe et al. | 106/417 |

FOREIGN PATENT DOCUMENTS 0 649 816 A  4/1995  European Pat. Off. .

OTHER PUBLICATIONS

Derwent Abstract AN 89–353145 of JP01–264932, Oct. 1989.

*Primary Examiner*—Mark L. Bell
*Assistant Examiner*—Scott L. Hertzog
*Attorney, Agent, or Firm*—Millen, White, Zelano & Branigan, P.C.

[57] ABSTRACT

Plateletlike, substrate-free titanium dioxide pigment obtainable by solidifying an aqueous solution of a thermally hydrolyzable titanium compound on a continuous belt, detaching the resulting layer, coating the resulting titanium dioxide platelets, with or without drying in between, with further titanium dioxide by a wet method, and separating off, drying and calcining the material obtained.

16 Claims, 1 Drawing Sheet

PLATELET-SHAPED TITANIUM DIOXIDE PIGMENT

The invention relates to a very thin titanium dioxide pearl luster pigment based on platelet-shaped titanium dioxide.

Pearl luster pigments containing titanium dioxide have been successfully employed for many years. They are constructed in accordance with the layer substrate principle, with mica being employed virtually without exception as substrate.

Two major processes are known for the precipitation of the $TiO_2$ layer. Firstly, precipitation can be carried out, as described for example in U.S. Pat. No. 3,087,828, by adding a solution of titanyl sulfate, acidified with sulfuric acid, to the mica suspension and carrying out hydrolysis by heating to about 100° C., with the layer thickness and the associated interference color being predetermined by the amount of titanyl sulfate present.

Secondly, precipitation can be carried out as described, for example, in German Patent 20 09 566. In that case, a mica suspension is heated to about 50°–100° C., especially 70°–80° C., an aqueous titanium salt solution is added slowly, and a substantially constant pH of about 0.5–5, in particular about 1.5–2.5, is maintained by simultaneous metered addition of a base, such as aqueous ammonia solution or an aqueous alkali metal hydroxide solution, for example. As soon as the desired layer thickness of the $TiO_2$ precipitate has been reached, the addition of the titanium salt solution is stopped.

A disadvantage of mica is that in the course of formation of titanium dioxide it induces the anatase modification although what is frequently desired is the rutile modification, which possesses a higher refractive index and further advantageous properties. It is therefore necessary to bring about the rutile modification by adding foreign ions, especially tin(IV) ions.

Processes of this kind are described, for example, in German Patents 22 14 545 and 25 22 572, where rutilization is brought about by incorporating tin dioxide in the vicinity of the mica or in discrete layers between the $TiO_2$. However, other processes are also known, for example the incorporation of zinc oxide in accordance with CS Patent 208,578 or the incorporation of iron(III) into the $TiO_2$ layer in accordance with DE-C 19 59 998, these processes leading to rutile layers.

Mica pigments are used widely in the printing and coating industries, in cosmetology and in polymer processing. They are distinguished by interference colors and a high luster. For the formation of extremely thin layers, however, mica pigments are not suitable, since the mica itself, as a substrate for the metal-oxide layers of the pigment, has a thickness of from 200 to 1200 nm. A further disadvantage is that the thickness of the mica platelets within a certain fraction defined by the platelet size in some cases varies markedly about a mean value. Moreover, mica is a naturally occurring mineral which is contaminated by foreign ions. Furthermore, technically highly complex and time-consuming processing steps are required, including, in particular grinding and classifying.

Pearl luster pigments based on thick mica platelets and coated with metal oxides have, owing to the thickness of the edge, a marked scatter fraction, especially in the case of relatively fine particle-size distributions below 20 μm.

As a substitute for mica it has been proposed to use thin glass flakes which are obtained by rolling a glass melt with subsequent grinding. Indeed, interference pigments based on such materials exhibit color effects superior to those of conventional, mica-based pigments. Disadvantages, however, are that the glass flakes have a very large mean thickness of about 10–15 μm and a very broad thickness distribution (typically between 4 and 20 μm), whereas the thickness of interference pigments is typically not more than 3 μm.

EP 0 384 596 describes a process in which hydrated alkali metal silicate is subjected at temperatures of 480°–500° C. to the action of an air jet, forming bubbles with thin walls; the bubbles are subsequently comminuted to give platelet-shaped alkali metal silicate substrates with a thickness of less than 3 μm. However, the process is complex and the thickness distribution of the resulting platelets is relatively broad.

DE 11 36 042 describes a continuous belt method of preparing platelet-shaped or glitter-like oxides or oxide hydrates of metals of groups IV and V and of the iron group of the periodic table. In this method, a release layer comprising, for example, a silicone coating is first of all applied, if desired, to a continuous belt in order to facilitate the subsequent detachment of the metal oxide layer. Then a liquid film is applied which comprises a solution of a hydrolysable compound of the metal which is to be converted into the desired oxide, and the film is dried and subsequently detached using a vibration device. The layer thickness of the platelets obtained is given as being 0.2 to 2 μm, although no concrete examples of this are cited.

EP 0 240 952 and EP 0 236 952 propose a continuous belt method of preparing various platelet-shaped materials, including silicon dioxide, aluminum oxide and titanium dioxide. In this method, a thin liquid film of defined thickness of a precursor of the platelet-shaped material is applied, via a roller system, to a smooth belt; the film is dried and detached from the belt, forming platelet-shaped particles. The particles are subsequently, if desired, calcined, ground and classified.

The thickness of the platelets obtained in accordance with the method described in EP 0 240 952 is relatively well defined, since the film is applied very uniformly, via a roller system, to the continuous belt, for example. The layer thickness of the platelets is given in the examples as being 0.3 to 3.0 μm. According to Example 1, a first roller is wetted with the precursor used by immersing this roller partially into a stock container which is filled with the precursor. The film is transferred from this roller to a second, corotating roller which is in very close contact with the first roller. Finally, the film is rolled off from the second roller onto the continuous belt.

Disadvantages, however, are the use of very expensive precursor materials and, in particular, the increased requirements in terms of workplace safety which must be applied when organometallic compounds are used. The complete chemical conversion of the precursor into the desired layer material requires, in general, high heating of the film and of the belt material. In addition to the considerable thermal stress which this places on the belt material, the high energy consumption and the restriction on process speed are highly disadvantageous for the economy of the method.

WO 93/08237 describes platelet-shaped pigments consisting of a platelet-shaped matrix comprising silicon dioxide, which may contain soluble or insoluble colorants and which is colored with one or more reflecting layers of metal oxides or metals. The platelet-shaped matrix is prepared by solidification of waterglass on a continuous belt.

DE 12 73 098 describes the preparation of a mother-of-pearl pigment by vapor deposition of ZnS, $MgF_2$, ZnO, $CaF_2$ and $TiO_2$ films onto a continuous belt. This process, however, like the process described in U.S. Pat. No. 4,879, 140 in which platelet-shaped pigments with Si and $SiO_2$ layers are obtained by plasma deposition from $SiH_4$ and $SiCl_4$, is associated with very high expenditure on apparatus.

Despite numerous attempts, it has not hitherto been possible to develop any economic process for preparing very thin platelet-shaped titanium dioxide pigments having a layer thickness of less than 500 nm.

The object of the invention is to provide a highly luster pearl luster pigment of titanium dioxide having a layer thickness of less than 500 nm and a layer thickness tolerance of less than 10%, where the pigment contains virtually no foreign ions and is in the rutile or the anatase form.

This object is achieved in accordance with the invention by a platelet-shaped, substrate-free titanium dioxide pigment obtainable by solidifying an aqueous solution of a thermally hydrolysable titanium compound on a continuous belt, detaching the resulting layer, coating the resulting titanium dioxide platelets, with or without drying in between, with further titanium dioxide by a wet method, and separating off, drying and calcining the material obtained.

The thermally hydrolzyable titanium compound used preferably takes the form of an aqueous titanium tetrachloride solution. The concentration of the titanium salt in these solutions is from 7 to 30% by weight, preferably from 8 to 15% by weight.

This object is additionally achieved in accordance with the invention by a process for preparing the novel pigment, in which a precursor of the platelet-shaped titanium dioxide is applied as a thin film to a continuous belt, the liquid film is solidified by drying, in the course of which the titanium dioxide is developed from the precursor by means of a chemical reaction, the resulting layer is subsequently detached from the belt and washed, the titanium dioxide platelets obtained, with or without drying in between, are suspended in water and coated with further titanium dioxide, and the coated titanium dioxide platelets are separated off from the aqueous suspension, dried and, if desired, calcined.

After drying, the titanium dioxide is in the anatase modification. By calcining above 600° C. it can be converted without the presence of foreign ions into the rutile form. By this means a highly pure titanium dioxide pigment in the rutile form is obtained which is superior in many respects to the conventional titanium dioxide pigments based on mica.

If tin is incorporated into the $TiO_2$ matrix, then transformation to the rutile form in fact takes place in the course of drying, from 110° C.

The invention additionally relates to the use of the novel pigment for pigmenting paints, printing inks, plastics, cosmetics and glazes for ceramics and glass.

For this purpose they can also be employed as mixtures with commercially available pigments, for example inorganic and organic absorption pigments, metal-effect pigments and LCP pigments.

The novel pigment consists of platelet-shaped titanium dioxide. These platelets have a thickness of between 10 and 500 nm, preferably between 40 and 300 nm. The extent in the two other dimensions is between 2 and 200 $\mu$m and, in particular, between 5 and 50 $\mu$m.

The novel pigment is prepared in a two-stage process. In the first stage, titanium dioxide platelets are produced with the aid of a continuous belt.

BRIEF DESCRIPTION OF THE DRAWING

First of all, the belt method will be explained with reference to FIG. 1.

The continuous belt 1, which is guided via a roller system 2, passes through an applicator unit 3 in which it is coated with a thin film of the precursor. Suitable applicator units which can be employed are roller applicators and also flow-type units. The belt speed is between 2 and 400 m/min, preferably 5–200 m/min.

Figure 1:
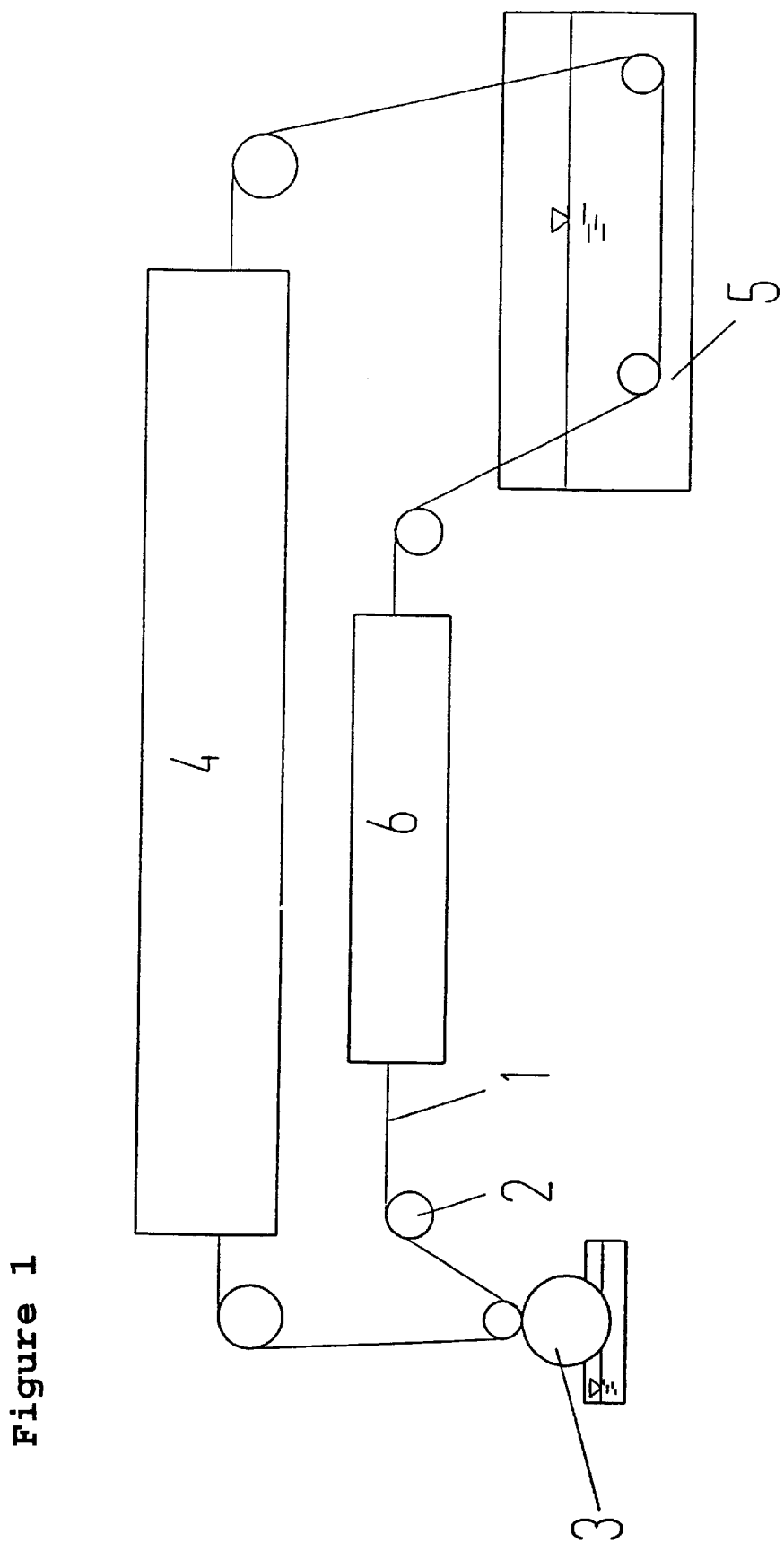

In order to achieve uniform wetting of the plastics belt it is expedient to add a commercially available wetting agent to the coating solution or to activate the surface of the belt by flame treatment, corona treatment or ionization.

The coated belt passes subsequently through a drying section 4 in which the layer is dried at temperatures between 30° and 200° C. As driers it is possible, for example, to employ commercially available infrared, circulating-air jet and UV driers.

After passing through the drying section, the belt is passed through the detachment baths 5 containing an appropriate detachment medium, for example fully deionized water, where the dried layer is removed from the belt. This detachment procedure is supported by additional devices, for example jets, brushes or ultrasound.

In a subsequent drier 6, the belt is dried before being coated again.

The continuous belt should be made from a chemically and thermally resistant plastic in order to ensure an adequate service life and high drying temperatures. Suitable materials for the belt include polyethylene terephthalate (PET) or other polyesters and polyacrylates.

The film width is typically between a number of centimeters and two or more meters. The thickness is between 10 $\mu$m and a number of millimeters, these two parameters being optimized in respect of the particular requirements.

Further details of continuous belt methods are known from U.S. Pat. No. 3,138,475, EP 0 240 952 and WO 93/08237.

In a second process stage, the titanium dioxide platelets detached from the belt are coated, without being dried beforehand, with further titanium dioxide in accordance with known methods. It is preferred to use the method described in U.S. Pat. No. 3,553,001.

An aqueous titanium salt solution is added slowly to a suspension of the titanium dioxide platelets which is heated at about 50°–100° C., especially 70°–80° C., and a substantially constant pH of about 0.5–5, in particular about 1.5–2.5, is maintained by simultaneous metered addition of a base, for example aqueous ammonia solution or an aqueous alkali metal hydroxide solution. As soon as the desired layer thickness of the $TiO_2$ precipitate has been reached, the addition of the titanium salt solution is stopped.

This method, which is also called the titration method, is notable for the fact that it avoids an excess of titanium salt. This is achieved by supplying to the hydrolysis, per unit time, only that amount (of titanium salt) as is required for uniform coating with the hydrated $TiO_2$ and as can be adsorbed per unit time by the available surface of the particles to be coated. There is, therefore, virtually no formation of hydrated titanium dioxide particles which are not deposited on the surface to be coated. The amount of titanium salt added per minute is, in this case, in the order of from about 0.01 to $2 \cdot 10^{-4}$ mol of titanium salt per square meter of surface to be covered.

Furthermore, in addition, the titanium dioxide platelets can also be coated with further titanium dioxide, after drying, in a fluidized-bed reactor by means of gas-phase coating, in which case, for example, the techniques proposed in EP 0 045 851 and EP 0 106 235 for preparing pearl luster pigments can be employed appropriately.

The novel pigment can in addition be coated with firmly adhering inorganic or organic colorants of low solubility. It is preferred to use color lakes and, in particular, aluminum colored lakes. To this end an aluminum hydroxide layer is applied by precipitation and in a second step is laked with a color lake. The process is described in more detail in DE 24 29 762 and DE 29 28 287.

Also preferred is additional coating with complex salt pigments, especially cyanoferrate complexes, for example Prussian blue and Turnbull's blue, as is described in EP 0 141 173 and DE 23 13 332.

The novel pigment can also be coated with organic dyes and, in particular, with phthalocyanine or metal phthalocyanine and/or indanthrene dyes according to DE 40 09 567. For this purpose a suspension of the pigment in a solution of the dye is prepared, and this suspension is then brought together with a solvent in which the dye is of low or zero solubility.

For an additional coating it is also possible, furthermore, to employ chalcogenides or metal chalcogenide hydrates and carbon black.

It is additionally possible to subject the pigment to an aftercoating or aftertreatment which further increases the light stability, weathering resistance and chemical stability or facilitates the handling of the pigment, especially its incorporation into different media. Examples of suitable aftercoating and/or aftertreatment techniques are those described in DE-C 22 15 191, DE-A 31 51 354, DE-A 32 35 017 or DE-A 33 34 598.

The additionally applied substances make up only about from 0.5 to 5% by weight, preferably from about 1 to 3% by weight, of the overall pigment.

The pigment can be used in conventional manner for pigmenting foods, paints, printing inks, plastics, cosmetics and glazes for ceramics and glass. However, it can also be employed for UV protection in cosmetic formulations or for industrial applications, since it screens out virtually all of the ultraviolet radiation in the range below 330 nm. Consequently, the pigment is markedly superior to the photoprotective filters available commercially.

The concentration of the pigment in these formulations is from 0.1% to 30% by weight, preferably from 1 to 10% by weight.

The screening action of the novel pigment in respect of UW radiation was compared with that of Luxelen Silk D (manufacturer: Presperse, Inc.), a commercially available sunscreen. For this purpose the pigment (layer thickness: 130 nm) and the comparison product were incorporated into an NC lacquer (pigment concentration 1.7%) which was knife-coated onto a glass plate. After drying, the films were detached from the substrate and were measured using a PE Lambda 19 instrument with built-in integration sphere (enlarged Specacarol diaphragms, 30 nm) for transmission, reflection and absorption in the range from 200 to 2500 nm. The transmission of the film containing the novel pigment is 0% below 330 nm, about 5% at 350 nm, 35% at 380 nm and 40% at 400 nm. The permeability for UV radiation below 350 nm is therefore much less than that of the comparison product.

In terms of thickness, the novel pigment represents the ideal state which is the most which can be achieved with pearl luster pigments.

In the present case the platelet thickness corresponds to the required layer thickness for the optically functional $TiO_2$ layer, whereas in the case of conventional pearl luster pigments the platelet thickness may be greater by a factor of 25, since the layer thickness of the substrate, for example mica, is added to the functional layer.

In terms of the technical applications this results in intrinsic advantages which can be achieved by no other conventional pearl luster pigment.

For example, coats of paint can be made thinner and the quantity of pigment required can be reduced since, owing to the absence of the support material "filler", the pigments are optically more efficient.

The examples which follow are intended to illustrate the invention without limiting it.

EXAMPLE 1

A circulating belt of polyethylene terephthalate (width: 0.3 m, speed: 20 m/min) is coated with a 20% titanium tetrachloride solution by means of a counter-rotating applicator roll. The coating solution contains 0.3% by weight of a surfactant (DISPERSE-AYD W-28, manufacturer: DANIEL PRODUCTS COMPANY). The aqueous film on the belt is dried in a drying section by subjecting it to hot air at 70° C. and the layer formed is detached from the belt in a detachment basin filled with fully deionized water. The titanium dioxide particles are filtered and are washed with fully deionized water. The platelets have a silvery luster and a layer thickness of 100±10 nm. For coating with further titanium dioxide, they are redispersed in fully deionized water.

2 l of the dispersion of $TiO_2$ platelets (solids content: 15 g of $TiO_2$) from Example 1 are heated to 75° C. and adjusted with dilute hydrochloric acid to a pH of 2.2.

A 40% aqueous titanium tetrachloride solution is then metered in at a rate of 3 ml/min and the pH is still kept constant at 2.2 using 32% NaOH.

Addition of $TiCl_4$ is continued until the desired first- or higher-order interference color is reached. The pigment obtained is filtered off, washed with deionized water until salt-free, dried and calcined at 750° C. The color properties do not alter greatly as a function of the calcination temperature, in which context the anatase-rutile transformation, which begins at about 600° C. and is over at 750° C., plays an important role.

EXAMPLE 2

| | Sun protection cream | |
|---|---|---|
| Constituents | | |
| Component A: | Liquid paraffin | 20.0% |
| | Cetyl alcohol | 1.5% |
| | Beeswax | 6.0% |
| | Stearic acid | 20.0% |
| | PEO (5.5) cetyl ether | 1.5% |
| | Sorbitol monostearate | 2.5% |
| Component B: | 10% NaOH | 1.0% |
| | Distilled water | 36.5% |
| Component C: | Glycerol | 6.0% |
| | $TiO_2$ pigment | 5.0% |

Preparation

The pigment is dispersed in glycerol. Components A and B are heated separately to 75° C. and are blended in gel form with the aid of a high-speed stirrer. Finally, component C is emulsified in the emulsion of A and B at 50° C.

We claim:

1. Platelet shaped, substrate-free titanium dioxide pigment obtainable by solidifying an aqueous solution of a thermally hydrolysable titanium compound on a continuous belt, detaching the resulting layer, coating the resulting titanium dioxide platelets, with or without drying in between, with further titanium dioxide by a wet method, and separating off, drying and calcining the material obtained.

2. Titanium dioxide pigment according to claim 1, characterized in that the thermally hydrolysable titanium compound employed is an aqueous titanium tetrachloride solution.

3. Process for the preparation of the titanium dioxide pigment according to claim 1, characterized in that
   an aqueous solution of a thermally hydrolysable titanium compound is applied as a thin film to a continuous belt,
   the liquid film is solidified by drying, in the course of which the titanium dioxide is developed from the solution by means of a chemical reaction,
   the resulting layer is subsequently detached from the belt and washed,
   the titanium dioxide platelets obtained, with or without drying in between, are suspended in water and coated with further titanium dioxide, and
   the titanium dioxide platelets are separated off from the aqueous suspension, dried and, optionally, calcined.

4. The process according to claim 3, characterized in that the aqueous solution of a thermally hydrolysable titanium compound employed is an aqueous titanium tetrachloride solution.

5. Process according to claim 3, characterized in that the additional titanium dioxide is applied to the dried titanium dioxide platelets in a fluidized-bed reactor by means of CVD.

6. A method comprising incorporating the pigments according to claim 1 in paints, printing inks, plastics, cosmetics and glazes for ceramics and glass and in foodstuffs and sunscreens.

7. The method according to claim 6, characterized in that the pigments are employed in the form of a mixture of pigments.

8. Paint, printing ink, plastic, cosmetic, ceramic or glass pigmented with a pigment according to claim 1.

9. The pigment of claim 1, which has a layer thickness of 500 nm.

10. The pigment of claim 9, which has a layer thickness tolerance of less than 10%.

11. The pigment of claim 2, wherein the concentration of the titanium tetrachloride in the solution is from 7 to 30% by weight.

12. The pigment of claim 1, which is calcined at above 600° C. and is in rutile form.

13. The pigment of claim 1, which has a thickness of between 40 and 300 nm.

14. The process of claim 3, wherein the drying is conducted at temperatures between 30° and 200° C.

15. The process of claim 3, wherein the coating with further titanium dioxide is conducted by adding an aqueous titanium salt solution to a suspension of the titanium dioxide platelets heated to about 50°–100° C. and at a substantially constant pH of 0.5–5.

16. The method of claim 6, wherein 0.1 to 30% by weight of the pigment is incorporated.

* * * * *